United States Patent [19]

Na et al.

[11] Patent Number: 5,346,702
[45] Date of Patent: Sep. 13, 1994

[54] USE OF NON-IONIC CLOUD POINT MODIFIERS TO MINIMIZE NANOPARTICLE AGGREGATION DURING STERILIZATION

[75] Inventors: George C. Na, Fort Washington; Natarajan Rajagopalan, Phoenixville, both of Pa.

[73] Assignee: Sterling Winthrop Inc., New York, N.Y.

[21] Appl. No.: 985,424

[22] Filed: Dec. 4, 1992

[51] Int. Cl.$^5$ .......................... A61K 9/14; A61K 9/54
[52] U.S. Cl. .......................... 424/490; 424/2; 424/4; 424/491; 424/492; 424/493; 424/494; 424/496; 424/497; 424/498; 424/5; 514/970; 514/971; 514/975
[58] Field of Search ............... 424/490, 493, 494, 497, 424/498, 499

[56] References Cited
U.S. PATENT DOCUMENTS 5,145,684  1/1991  Liversidge et al. ................. 424/489

FOREIGN PATENT DOCUMENTS 498482  12/1992  European Pat. Off. .

*Primary Examiner*—Thurman K. Page
*Assistant Examiner*—James M. Spear
*Attorney, Agent, or Firm*—William J. Davis

[57] ABSTRACT

This invention discloses a composition comprised of nanoparticles having a surface modifier adsorbed on the surface thereof and a non-ionic cloud point modifier associated therewith, which cloud point modifier is present in an amount-sufficient to increase the cloud point of the surface modifier. A preferred surface modifier is a poloxamine such as Tetronic 908, and preferred non-ionic cloud point modifiers include polyethylene glycol, propylene glycol, ethanol, hydroxypropylcyclodextrin and/or glycerol. This invention further discloses a method of making nanoparticles having a surface modifier adsorbed on the surface and a non-ionic cloud point modifier associated therewith, comprised of contacting said nanoparticles with the cloud point modifier for a time and under conditions sufficient to increase the cloud point of the surface modifier.

14 Claims, 1 Drawing Sheet

USE OF NON-IONIC CLOUD POINT MODIFIERS TO MINIMIZE NANOPARTICLE AGGREGATION DURING STERILIZATION

FIELD OF THE INVENTION

This invention relates to therapeutic and diagnostic compositions with a modified cloud point, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

As a result of their small size, sterilization of therapeutic and diagnostic agents in nanoparticulate form stabilized by a surface modifier (surfactant) is difficult. Filtration using a filter of 0.22 μm mesh size is sufficient to remove most bacteria and viruses, but the nanoparticles, due to their sizes, cannot be sterile filtered. Conventional autoclaving (steam heat) at 121° C. will result in aggregation and/or substantial growth of particle size, rendering the resulting particles unusable.

The aggregation of nanoparticles upon heating is directly related to the precipitation of the surface modifier (surfactant) at temperatures above the cloud point of the surfactant where the bound surfactant molecules are likely to dissociate from the nanoparticles and precipitate, leaving the nanoparticles unprotected. The unprotected nanoparticles can then aggregate into clusters of particles. Upon cooling, the surfactant redissolves into the solution, which then coats the aggregated particles and prevent them from dissociating into smaller ones. See FIG. 1.

This invention is directed to novel compositions that allow autoclaving of nanoparticles with reduced or no particle size growth. These compositions provide for a modification of the surfactant adsorbed onto nanoparticles such that the nanoparticles do not-agglomerate during autoclaving. This invention is also directed to a method of making such compositions.

BRIEF SUMMARY OF THE INVENTION

This invention is directed to a composition comprised of nanoparticles having a surface modifier adsorbed on the surface thereof and a non-ionic cloud point modifier associated therewith, which cloud point modifier is present in an amount sufficient to increase the cloud point of the surface modifier.

This invention further discloses a method of making nanoparticles having a surface modifier adsorbed on the surface and a non-ionic cloud point modifier associated therewith, said method comprising contacting said nanoparticles with the cloud point modifier for a time and under conditions sufficient to increase the cloud point of the surface modifier.

DETAILED DESCRIPTION OF THE INVENTION

Figure 1:
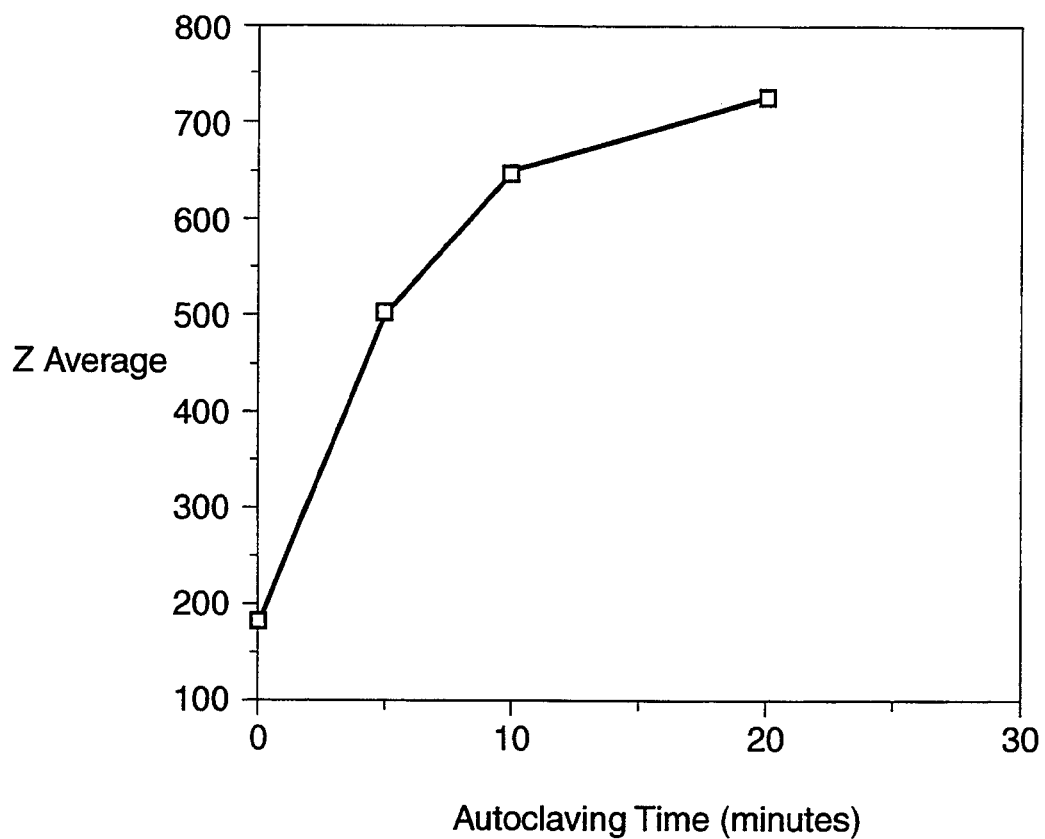
FIG. 1 is a graph showing the aggregation of nanoparticles comprised of 20 percent of the ethyl ester of diatrazoic acid and the surface modifier Tetronic 908 (T908) upon autoclaving at 120° C. Samples of the autoclaved nanoparticles were removed at various times after autoclaving, and the mean particle size (Z average) was determined for each time point.

This invention is directed to a composition comprised of nanoparticles having a surface modifier adsorbed on the surface thereof and a non-ionic cloud point modifier associated therewith, which cloud point modifier is present in an amount sufficient to increase the cloud point of the surface modifier. In a preferred embodiment, the cloud point of the surface modifier is increased above the temperature for autoclaving of the nanoparticles to prevent agglomeration.

The nanoparticles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants.

Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens TM, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986.

Particularly preferred surface modifiers include polyvinylpyrrolidone, tyloxapol, poloxamers such as Pluronic TM F68 and F108, which are block copolymers of ethylene oxide and propylene oxide, and poloxamines such as Tetronic TM 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT TM, which is a dioctyl ester of sodium sulfosuccinic acid, available from American Cyanamid, Duponol TM P, which is a sodium lauryl sulfate, available from DuPont, Triton TM X-200, which is an alkyl aryl polyether sulfonate, available from Rohm and Haas, Tween 80, which is a polyoxyethylene sorbitan fatty acid ester, available from ICI Specialty Chemicals, and Carbowax TM 3350 and 934, which are polyethylene glycols available from Union Carbide. Surface modifiers which have been found to be particularly useful include Tetronic 908, the Tweens ™, Pluronic F-68 and polyvinylpyrrolidone. Other useful surface modifiers include:

decanoyl-N-methylglucamide;
    n-decyl β-D-glucopyranoside;
    n-decyl β-D-maltopyranoside;
    n-dodecyl β-D-glucopyranoside;
    n-dodecyl β-D-maltoside;
    heptanoyl-N-methylglucamide
    n-heptyl β-D-glucopyranoside;
    n-heptyl β-D-thioglucoside;
    n-hexyl β-D-glucopyranoside;
    nonanoyl-N-methylglucamide;
    n-nonyl β-D-glucopyranoside;
    octanoyl-N-methylglucamide;
    n-octyl β-D-glucopyranoside;
    octyl β-D-thioglucopyranoside;

and the like.

The surface modifiers are commercially available and/or can be prepared by techniques known in the art. Two or more surface modifiers can be used in combination.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684 and EP-A 498,482, whose disclosures are incorporated herein by reference. A preferred diagnostic agent is the x-ray imaging agent WIN-8883 (ethyl 3,5-diacetoamido-2,4,6-triiodobenzoate).

As used herein, particle size refers to a mean particle size as measured by conventional particle size measuring techniques well known to those skilled in the art, such as sedimentation field flow fractionation, photon correlation spectroscopy, or disk centrifugation. By "an effective average particle size of less than about 400 nm it is meant that at least 90% of the particles have a weight average particle size of less than about 400 nm" when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid media from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

As noted elsewhere herein, sterile filtration will not provide adequate sterilization for nanoparticles. Therefore, other methods of sterilization are required. For example, steam or moist heat sterilization at temperatures of about 121° C. for a time period of about 15 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

Sterilization takes place in the presence of non-ionic cloud point modifiers. Examples of suitable cloud point modifiers include polyethylene glycols, e.g., PEG 300, PEG 400, PEG-1000 and PEG 2000, available from J. T. Baker Chemical Co., propylene glycol, ethanol, hydroxypropylcyclodextrin, and/or glycerol which minimize particle growth during sterilization. A preferred cloud point modifier is PEG 400.

The cloud point is the temperature at which the surface modifier (surfactant) precipitates out of solution as described above. By the phrase "cloud point modifier" is meant a compound which influences the cloud point of surface modifiers. In particular, the cloud point modifiers useful in the present invention raise the cloud point of the surface modifiers found adsorbed onto nanoparticles. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

The non-ionic cloud point modifier can be present in an amount of 0.01–50%, preferably 0.05–30%, more preferably 0.1–20% by weight based on the total weight of the nanoparticle suspension.

This invention further discloses a method of making nanoparticles having a surface modifier adsorbed on the surface and a non-ionic cloud point modifier associated therewith, comprised of contacting said nanoparticles with the cloud point modifier for a time and under conditions sufficient to increase the cloud point of the surface modifier.

This method involves the preparation of therapeutic or diagnostic nanoparticles, as discussed elsewhere herein, and contacting those nanoparticles with a cloud point modifier. Contacting may be by admixing a suspension of nanoparticles with a solution of cloud point modifier, followed by sterilization at a temperature and for a time sufficient to effect sterilization of the nanoparticle suspension.

The following examples further illustrate the invention and are not to be construed as limiting of the specification and claims in any way.

EXAMPLE 1

Nanoparticles comprised of 20 percent of the ethyl ester of diatrizoic acid and the surface modifier Tetronic 908 (T908) were autoclaved at 120° C. Samples of the autoclaved nanoparticles were removed at various times after autoclaving, and the particle size (Z average) was determined for each time point.

The data are presented in FIG. 1. As the data indicate, autoclaving for 5 minutes at 120° C. results in an average particle size of about 500 nm. By 20 minutes, the average particle size is in excess of 700 nm.

EXAMPLE 2.

Determination of the effect of several additives on the cloud point of T-908.

In this experiment, the cloud point of a 1 percent solution of the surface modifier T-908 was measured in the presence of various concentrations of PEG-400, glycerol, ethanol, hydroxypropylcyclodextrin (HPCD) propylene glycol and NaCl. The cloud point measurements are shown in Table 1.

TABLE 1

| [PEG-400] % w/v | Cloud Pt °C. | [NaCl] % w/v | Cloud Pt °C. | [Glycerol] % w/v | Cloud Pt °C. |
|---|---|---|---|---|---|
| 0 | 106 | 0 | 106 | 0 | 106 |
| 0.1 | 107 | 0.1 | 103 | 0.1 | 106 |

TABLE 1-continued

| 1 | 110 | 0.3 | 96 | 0.3 | 106 |
| 2 | 113 | 0.5 | 92 | 0.4 | 105 |
| 4 | 116 | 0.8 | 87 | 0.6 | 105 |
| 6 | 118 | 1 | 83 | 0.8 | 105 |
| 8 | 122 | | | 1 | 107 |
| 10 | 125 | | | 1.5 | 107 |
| | | | | 2 | 107 |
| | | | | 2.5 | 107 |
| | | | | 3 | 108 |

| [Ethanol] % w/v | Cloud Pt °C. | [HPCD] % w/v | Cloud Pt °C. | [Propylene Glycol] % w/v | Cloud Pt °C. |
|---|---|---|---|---|---|
| 5 | 118 | 0.1 | 107 | 0.3 | 107 |
| 10 | 126 | 1 | 109 | 5 | 116 |

The results in Table 1 show that PEG-400 ethanol and propylene glycol can raise the cloud point of T-908, glycerol and HPCD have only moderate effect and NaCl lowers the cloud point of T-908 significantly.

EXAMPLE 3.

Effect of PEG-400 on the size growth of WIN-8883 nanoparticles on heating.

In this example, two samples of 20 percent WIN-8883 nanoparticles containing 2 percent T-908 were prepared. One sample consisted of 10% (w/v) WIN-8883 nanoparticles in water, and the other sample consisted of 10% (w/v) WIN-8883 nanoparticles in 5% PEG-400. The two samples were heated from 104° to 126° C. with 2° C. interval with a 5 minute dwell time at each temperature. Samples were withdrawn from the samples with a syringe and needle and used for particle size analysis. The data from these studies is presented in Table 2.

TABLE 2

| | Avg. Particle Size (nm) | | Polydispersity | |
|---|---|---|---|---|
| Temp. | Control | 5% PEG-400 | Control | 5% PEG-400 |
| 104 | 189 | 184 | 0.13 | 0.112 |
| 106 | 192 | 195 | 0.175 | 0.151 |
| 108 | 205 | 192 | 0.083 | 0.176 |
| 110 | | 194 | | 0.159 |
| 112 | 220 | 206 | 0.168 | 0.111 |
| 114 | 259 | 218 | 0.059 | 0.131 |
| 116 | 285 | 227 | 0.155 | 0.089 |
| 118 | 320 | 235 | 0.213 | 0.067 |
| 120 | 443 | 257 | 0.267 | 0.15 |
| 122 | 400 | 288 | 0.263 | 0.1 |
| 124 | 427 | 308 | 0.242 | 0.183 |
| 126 | 504 | 342 | 0.307 | 0.198 |

The data presented in Table 2 show that the average particle size does not increase in the presence of 5% PEG-400 nearly as much as the control sample prepared in water.

EXAMPLE 4

Effect of PEG-400 on WIN-8883 particle size upon autoclaving at 121° C. for 20 minutes Samples of 10% (w/v) WIN-8883 nanoparticles were prepared from stock 20% suspension. These samples contain concentrations of PEG-400 ranging from 0 to 10% (w/v %). These samples were then autoclaved at 121° C. for 20 min. The particle sizes of each sample were measured both before and after autoclaving. The data from these experiments is shown in Table 3.

TABLE 3

| [PEG-400] W/V % | Average Particle Size (nm) | |
|---|---|---|
| | After Autoclaving | Before Autoclaving |
| 0 | 1284 | 178 |
| 2.5 | 1053 | 182 |
| 5 | 541 | 182 |
| 7.5 | 412 | 184 |
| 10 | 325 | 183 |

The data shown in Table 3 show that increasing the concentration of PEG-400 can reduce the particle size growth of nanoparticles caused by autoclaving at 121° C. for 20 minutes.

EXAMPLE 5

Effect of PEG molecular weight on the cloud point of T-908.

In this experiment, the cloud point of a 1 percent solution of the surface modifier T-908 was measured in the presence of various types and concentrations of PEG. The cloud point measurements are shown in Table 4.

TABLE 4

| [PEG-1000] % w/v | Cloud Pt °C. | [PEG-8000] % w/v | Cloud Pt °C. | [PEG-3350] % w/v | Cloud Pt °C. |
|---|---|---|---|---|---|
| 2 | 123 | 2 | 116 | 7.5 | 124 |
| 5 | 124 | 5 | 119 | | |

The effect of the concentration of PEG-1000 on the particle size growth of WIN 8883 nanoparticles containing 1% T-908 was examined by measuring mean particle size after autoclaving at 121° C. for 20 minutes. The data is presented in Table 5.

TABLE 5

| [PEG-1000] % w/v | Average Particle Size (nm) |
|---|---|
| 2 | 428 |
| 5 | 274 |
| 7 | 235 |
| 10 | 233 |

The data shown in Table 4 indicate that PEG-1000 is more effective than PEG-8000 and PEG-3350 at raising the cloud point of T-908.

The data shown in Table 5 show that increasing the concentration of PEG-1000 can reduce the particle size growth of nanoparticles caused by autoclaving at 121° C. for 20 minutes. The foregoing specification, including the specific embodiments and examples is intended to be illustrative of the present invention and is not to be taken as limiting. Numerous other variations and modifications can be effected without departing from the true spirit and scope of the present invention.

We claim:

1. A composition comprised of nanoparticles containing a diagnostic or having a nonionic surfactant as a surface modifier adsorbed on the surface thereof and a non-ionic cloud point modifier associated therewith, which cloud point modifier is present in an amount of 0.01–50 % by weight based on the total weight of the composition and sufficient to increase the cloud point of the surface modifier wherein said nanoparticles are resistant to size growth when said composition is heat sterilized at 121° C. for 15 minutes.

2. The composition of claim 1 wherein said nanoparticles contain a diagnostic agent.

3. The composition of claim 2 wherein said diagnostic agent is ethyl 3,5-diacetoamido-2,4,6-triiodobenzoate.

4. A composition comprised of nanoparticles containing a diagnostic or therapeutic agent having a nonionic surfactant as a surface modifier adsorbed on the surface thereof and a nonionic cloud point modifier associated therewith, which cloud point modifier is selected from the group consisting of polyethylene glycol, propylene glycol, ethanol, hydroxypropylcyclodextrin, and glycerol and is present in an amount of 0.01–50% by weight based on the total weight of the composition and sufficient to increase the cloud point of the surface modifier above the sterilization temperature of the nanoparticles, wherein said nanoparticles are resistant to particle size growth when said composition is heat sterilized at 121° C. for 15 minutes.

5. The composition of claim 1 wherein said nonionic surfactant is a poloxamine.

6. The composition of claim 2 wherein said surface modifier is a poloxamine, said cloud point modifier is polyethylene glycol, and said diagnostic agent is ethyl 3,5-diacetoamido-2,4,6-triiodobenzoate 7. The composition of claim 1 wherein said cloud point modifier is selected from the group consisting of polyethylene glycol, propylene glycol, ethanol, hydroxypropylcyclodextrin and glycerol.

8. The composition of claim 1 in wherein said cloud point modifier increases the cloud point of said surface modifier above the sterilization temperature of the nanoparticles.

9. A method of making the composition of claim 1 comprised of contacting said nanoparticles with said cloud point modifier for a time and under conditions sufficient to increase the cloud point of the surface modifier.

10. The method of claim 9 further comprising the step of sterilizing said nanoparticle.

11. The method of claim 10 wherein said sterilizing is by steam heat autoclaving.

12. The composition of claim 1 wherein said nanoparticles contain a therapeutic agent.

13. The composition of claim 1 wherein said nanoparticles have a mean particle size of less than 400 nm.

14. The composition of claim 1 wherein said nonionic surfactant is selected from the group consisting of polyoxyethylene alkyl ethers, polyoxyethylene stearates, tyloxapol, poloxamers and poloxamines.

* * * * *

UNITED STATES PATENT AND TRADEMARK OFFICE
CERTIFICATE OF CORRECTION

PATENT NO. : 5,346,702
DATED : September 13, 1994
INVENTOR(S) : George C. Na and Natarajan Rajagopalan It is certified that error appears in the above-identified patent and that said Letters Patent is hereby corrected as shown below:

In column 8, claim 1, line 58, "diagnostic or " should read -- diagnostic or therapeutic agent --.

Signed and Sealed this

First Day of November, 1994

Attest:

Attesting Officer

BRUCE LEHMAN
Commissioner of Patents and Trademarks